United States Patent
Betzold et al.

(10) Patent No.: US 6,311,088 B1
(45) Date of Patent: Oct. 30, 2001

(54) DUAL-CHAMBER PACEMAKER WITH OPTIMIZED PVARP FOLLOWING EVENT THAT MAY DISRUPT AV SYNCHRONY

(75) Inventors: Robert A. Betzold, Fridley; Eduardo N. Warman, Maple Grove, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/290,967

(22) Filed: Apr. 13, 1999

(51) Int. Cl.$^7$ .................................................. A61N 1/362
(52) U.S. Cl. .................................................. 607/14
(58) Field of Search ........................................... 607/9, 14

(56) References Cited

U.S. PATENT DOCUMENTS

| | | |
|---|---|---|
| 4,108,148 | 8/1978 | Cannonn, III . |
| 4,303,075 | 12/1981 | Heilman et al. . |
| 4,428,378 | 1/1984 | Anderson et al. . |
| 4,503,857 | 3/1985 | Boute et al. . |
| 4,554,920 | 11/1985 | Baker, Jr. et al. . |
| 4,554,921 | 11/1985 | Boute et al. . |
| 4,788,980 | 12/1988 | Mann et al. . |
| 4,890,617 | 1/1990 | Markowitz et al. . |
| 4,920,965 | 5/1990 | Funke et al. . |
| 5,024,222 | 6/1991 | Thacker . |
| 5,097,832 | 3/1992 | Buchanan . |
| 5,123,412 | 6/1992 | Betzold . |
| 5,144,949 | 9/1992 | Olson . |
| 5,301,669 | 4/1994 | Duncan ..................... 607/9 |
| 5,354,319 | 10/1994 | Wyborny et al. . |
| 5,441,523 | 8/1995 | Nappholz ..................... 607/14 |
| 5,609,610 | 3/1997 | Nappholz ..................... 607/9 |
| 5,626,623 | 5/1997 | Kieval et al. . |

FOREIGN PATENT DOCUMENTS

| | | |
|---|---|---|
| 0 526 798 A1 | 7/1992 | (EP) . |
| 0 726 082 A2 | 7/1996 | (EP) . |

OTHER PUBLICATIONS

PCT International Search Report, PCT/US00/06054, Aug. 3, 2000, Medtronic, Inc., Docket No. P8420.01 WO.

*Primary Examiner*—William E. Kamm
(74) *Attorney, Agent, or Firm*—Girma Wolde-Michael; Reed A. Duthler

(57) ABSTRACT

A pacemaker and a method of employing a pacemaker to pace a patient's heart. The method of operation of the pacemaker includes defining a post ventricular atrial refractory period having a first duration responsive to ventricular events, during which period the pacemaker does not initiate timing of an AV delay responsive to detected atrial depolarizations and in response to events which a may disrupt AV synchrony, such as PVC's, mode changes and the like, defining a post ventricular atrial refractory period having a second duration less than the first duration. The shortened post ventricular atrial refractory period remains in effect only temporarily, for example for one cardiac cycle, and may be initiated on a ventricular event which is the disrupting event or immediately follows the disrupting event, or may be initiated following a later ventricular event.

26 Claims, 6 Drawing Sheets

DUAL-CHAMBER PACEMAKER WITH OPTIMIZED PVARP FOLLOWING EVENT THAT MAY DISRUPT AV SYNCHRONY

FIELD OF THE INVENTION

The present invention relates to implantable dual chamber pacemakers, including rate responsive pacemakers, and to an improved response to premature ventricular contractions (PVCs) and other events which may disrupt the timing of pacing functions.

BACKGROUND OF THE INVENTION

Atrial synchronized dual chamber pacing modes, particularly, the multi-programmable, VDD, VDDR, DDD and DDDR pacing modes, have been widely adopted in implantable dual chamber pacemakers for providing atrial and ventricular or AV synchronized pacing on demand. A pacemaker implantable pulse generator (IPG) capable of pacing in atrial synchronized modes typically includes an atrial sense amplifier to detect atrial depolarizations or P-waves and generate an atrial sense event (A-SENSE) signal, a ventricular sense amplifier to detect ventricular depolarizations or R-waves and generate a ventricular sense event (V-SENSE) signal, a ventricular pacing pulse generator and for DDD or DDDR mode pacing an atrial pacing pulse generators as well, providing ventricular and atrial pacing (V-PACE and A-PACE) pulses, respectively, and an operating system governing pacing and sensing functions. The IPG supplies a V-PACE pulse to the ventricles through an appropriate lead system if the ventricles fail to depolarize on their own during an AV delay timed from a preceding A-SENSE or generation of an A-PACE pulse. In DDD or DDDR mode pacing If the atria fail to spontaneously beat within a pre-defined time interval (atrial escape interval), the pacemaker also supplies an A-PACE pulse to the atria through an appropriate lead system. Such AV synchronous pacemakers which perform this function have the capability of tracking the patient's natural sinus rhythm and preserving the hemodynamic contribution of the atrial contraction over a wide range of heart rates. Maintenance of AV mechanical synchrony is of great importance as set forth in greater detail in commonly assigned U. S. Pat. No. 5,626,623, incorporated herein by reference in its entirety.

Typically, the IPG comprises a microcomputer controlled, digital controller/timer circuit that defines and times out a V-A interval (in DDD and DDDR modes) or a V-V interval (in VDD and VDDR modes) upon a V-SENSE or V-PACE pulse and times out an AV delay in response to an A-SENSE (in VDD, VDDR, DDD, DDDR modes) or in response to an A-PACE pulse (in DDD and DDDR modes) as well as a number of other intervals. In some DDD and DDDR mode pacers, separate AV delays are commenced by the A-SENSE signal (an SAV delay) and the A-PACE pulse (a PAV delay).

Additional intervals timed by the IPG include atrial and ventricular sense amplifier blanking periods following delivery of a atrial and/or ventricular pacing pulses to disable atrial and ventricular amplifier sensing. In addition, a number of sense amplifier refractory periods are timed out on atrial and ventricular sense event signals and generation of A-PACE and V-PACE pulses, whereby "refractory" A-SENSE and V-SENSE signals during such refractory periods are selectively ignored or employed in a variety of ways to reset or extend time periods being timed out. Atrial and ventricular refractory periods (ARP and VRP) are commenced upon an A-SENSE or V-SENSE signal or generation of an A-PACE or V-PACE pulse, respectively. The ARP extends through the SAV delay or the PAV delay until a certain time following a V-SENSE signal terminating the SAV or PAV delay or generation of a V-PACE pulse at the expiration of the SAV or PAV delay.

In addition, a post-ventricular atrial refractory period (PVARP) is commenced by a V-PACE pulse or V-SENSE based on the understanding that A-SENSE signals sensed during its time-out generally reflect a retrograde conduction of the evoked or spontaneous ventricular depolarization wave and therefore are not employed to reset an escape interval and commence an SAV delay. The duration of PVARP may be fixed or vary as a function of sensed atrial rate or pacemaker defined pacing rate, with the result that in many cases relatively long PVARPs are in effect at lower rates.

The rate-adaptive VDDR and DDDR pacing modes function in the above-described manner but additionally provide rate modulation of a pacing escape interval between a programmable lower rate and an upper rate limit (URL) as a function of a physiologic signal or rate control parameter (RCP) related to the need for cardiac output developed by a physiologic sensor. At times when the intrinsic atrial rate is inappropriately high or low, a variety of "mode switching" schemes for effecting switching between tracking modes and non-tracking modes (and a variety of transitional modes) based on the relationship between the atrial rate and the sensor derived pacing rate have been proposed as exemplified by commonly assigned U.S. Pat. No. 5,144,949, incorporated herein by reference in its entirety.

The disruption of AV electrical and mechanical synchrony frequently arises due to the spontaneous depolarization of the ventricles triggered at an ectopic site in one of the ventricles. Such a spontaneous depolarization that is not associated with a prior atrial depolarization is characterized as a premature ventricular contraction (PVC). Many of the problems resulting from the occurrence of a PVC in a patient with a dual chamber pacemaker are described more fully in U.S. Pat. Nos. 4,788,980 and 5,097,832, both of which are incorporated herein by reference. One such problem is the initiation of pacemaker mediated tachycardias or PMTs. The most commonly employed PVC response to prevent initiation of PMTs is to extend the PVARP to a programmed duration, such as 400–500 msec., in response to the PVC, thus masking atrial sense signals that are presumed to result from retrograde conduction during this period of time as disclosed in the above-incorporated '980 patent. Numerous other patents have dealt with varying the PVARP in an attempt to prevent instigating a PMT, including U.S. Pat. Nos. 4,920,965, 4,554,921, 5,123,412, and 4,503,857, all incorporated herein by reference in their entireties.

Unfortunately, in some circumstances prolongation of the PVARP in response to a PVC has unfortunate consequences. Even though a possible PMT is prevented, loss of normal P-wave tracking may occur because the next P-wave is masked by the PVC response. Subsequent R-waves occurring prior to the time of the next scheduled atrial pacing pulse or non-refractory sensed atrial depolarization in DDD and DDDR modes or prior to the next scheduled ventricular pacing pulse or non-refractory sensed atrial depolarization in VDD or VDDR modes initiate a subsequent PVARP. If the subsequent PVARP is long enough, the next P-wave may fall therein and fail to initiate an A-V delay. Loss of atrial synchrony may extend over a period of seconds to hours depending on the pacemaker's programmed rate settings and the patient's sinus rate (i.e., the P-wave rate set by the SA node). Ventricular pacing remains inhibited until either the occurrence of a non-refractory sensed atrial depolarization (VDD, VDDR, DDD, or DDDR mode pacers), delivery of an atrial pacing pulse (ODD or DDDR mode pacers) or delivery of a ventricular pacing pulse on lower rate time-out (VDD or VDDR mode pacers).

A similar problem may arise in response to other events which disrupt AV synchrony. Additional events which disrupt AV synchrony can include premature atrial contractions, noise sensing and associated asynchronous pacing, also io known as "noise reversion" and other pacing mode or operation changes, including those arising from mode switching, magnet application and removal, cancel magnet commands, device programming and downlink telemetry functions. In particular, changes from non-atrial synchronized pacing modes to atrial synchronized pacing modes or from non-atrial synchronized operation to atrial synchronized operation within an atrial synchronized pacing mode have the potential to disrupt AV synchrony. Prolongation of PVARP in response to such other disrupting events is disclosed in U.S. Pat. No. 4,554,920, also incorporated herein by reference in its entirety.

In modern dual chamber pacemakers, the current PVARP may vary as a function of programming and/or vary between minimum and maximum PVARPs as a function of current pacing rate or sensed atrial rate. In the context of pacemakers which employ PVARPs which vary as a function of pacing rate or sensed atrial rate, the relatively long PVARPs which may be in effect at lower rates can in the same fashion result in persistent loss of AV synchrony due to PVCs or other disrupting events even in the absence of extension of the PVARP.

What is needed, therefore, is a system for avoiding the persistent loss of AV synchrony resulting from temporary disruption of AV synchrony while retaining the ability to avoid pacemaker mediated tachycardias.

SUMMARY OF THE INVENTION

In accordance with the present invention, persistent loss of AV synchrony is avoided by providing a response to PVCs and other events which disrupt AV synchrony that allows a subsequent intrinsic atrial depolarization to be sensed outside the refractory period and to re-synchronize the cardiac cycles timed by the pacemaker IPG to an atrial depolarization.

In a VDD, VDDR, DDD or DDDR pacing mode, the response to a PVC or other disrupting event is to temporarily (e.g. for one cardiac cycle only) provide a PVARP of appropriate duration starting either with the current cardiac cycle or following a ventricular event initiating a subsequent cardiac cycle, to allow subsequent atrial depolarizations to be sensed and employed to re-synchronize the cardiac cycles timed by the pacemaker IPG to a atrial depolarizations In one embodiment of the invention, the shortened PVARP is calculated in response to a PVC or other disrupting event only when the current PVARP is greater than or equal to a first defined duration greater than the minimum PVARP. The shortened PVARP may be calculated as a function of the current PVARP or may be of fixed duration equal to or different from the defined duration. The PVARP may be left un-altered if the current PVARP is less than the first defined duration. In some embodiments, the PVARP may be extended if the current PVARP is less than a second defined duration less than the first duration, in order to prevent occurrence of PMTs.

The shortened PVARP provided in response to a PVC may be commenced upon sensing the PVC or alternatively may be commenced upon a subsequent ventricular event starting a subsequent cardiac cycle. In the event that the shortened PVARP is to be employed following the ventricular event initiating a subsequent cardiac cycle, the PVARP may first optionally be extended for the cardiac cycle initiated by the PVC, as is conventional.

If the disrupting event is not a PVC, the shortened PVARP may be commenced on the ventricular event initiating the next cardiac cycle or alternatively may be commenced upon a later ventricular event starting a subsequent cardiac cycle. In the event that the shortened PVARP is to be employed following the ventricular event initiating a subsequent cardiac cycle, the PVARP may first optionally be extended for the cardiac cycle initiated by the ventricular event immediately following the disrupting event.

The shortened PVARP allows for synchronization to spontaneous atrial depolarization that would otherwise be prevented by the current PVARP and allows the AV delay to be restarted. Thereafter, the current PVARP is restored to ensure that a PMT response is not initiated. The present invention advantageously restores synchronized cardiac output under specific circumstances while allowing relatively long maximum or base PVARPs to be programmed and employed to avoid the initiation of a PMT.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

Figure 1:
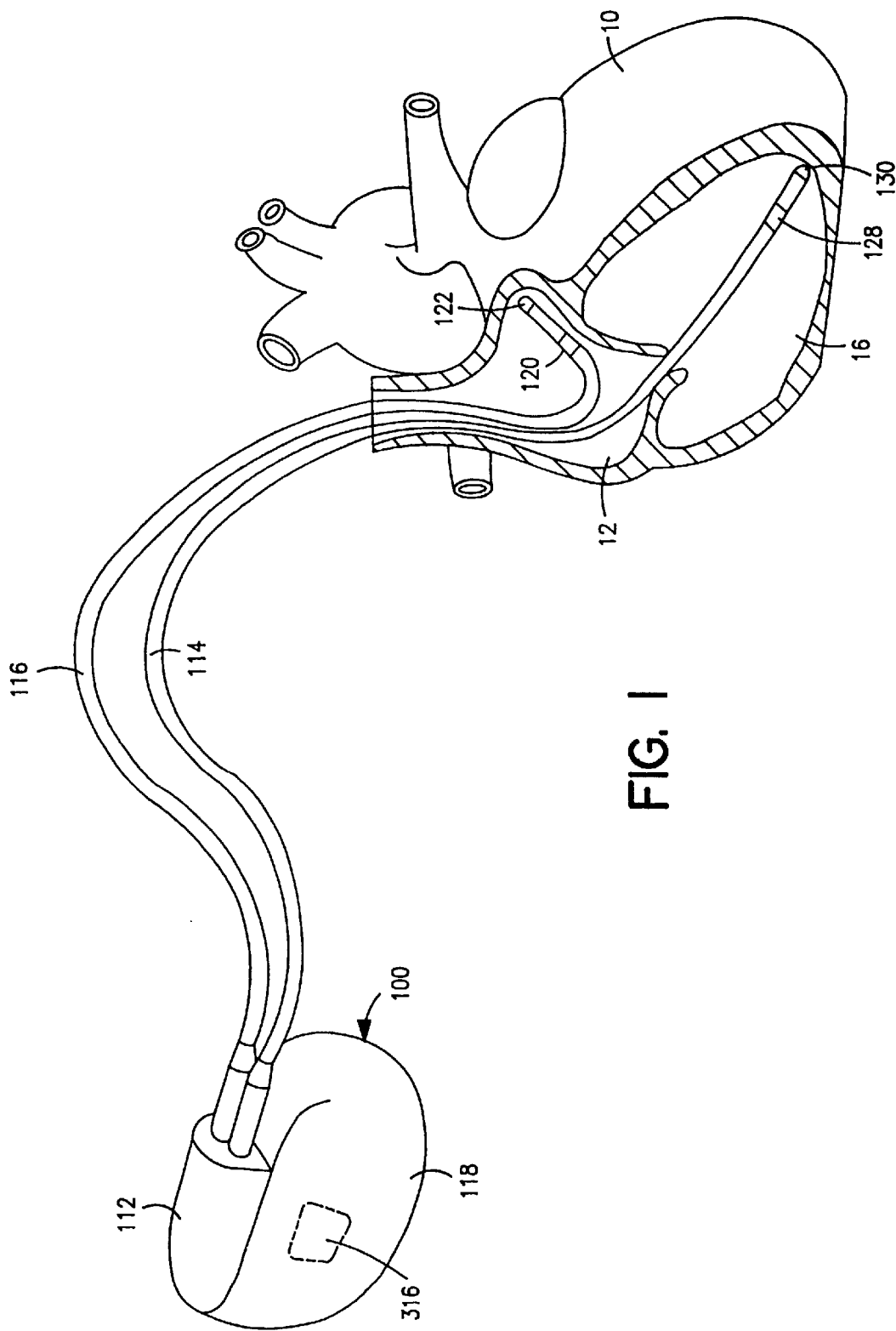
FIG. 1 is a view of one embodiment of an implantable pacemaker implanted subcutaneously in a patient's body in which the present invention is advantageously implemented.

FIG. 1 depicts the external configuration of a typical implantable dual chamber pacemaker, e.g. a VDD, VDDR, DDD or DDDR pacemaker, comprising dual chamber IPG 100 and unipolar or bipolar atrial and ventricular leads 114 and 116 (bipolar leads are depicted), in which the present invention may be implemented. The DDD and DDDR pacemaker IPGs sense and pace in the atrial and ventricular chambers, and pacing is either triggered and inhibited depending upon sensing of intrinsic, non-refractory atrial and ventricular depolarizations during the sequentially timed V-A interval and AV delay, respectively, as is well known in the art. Such DDD and DDDR pacemaker IPGs effectively function in a VDD pacing mode when the sinus atrial heart rate varies within the lower rate and the upper rate limit and such intrinsic atrial depolarizations are consistently sensed. The present invention can be implemented as well into VDD and VDDR pacemakers that are implanted in patients with healthy sinus atrial heart rates. The following description is thus intended to encompass all of the various types of dual chamber pacemaker systems in which the present invention can be implemented.

Figure 2:
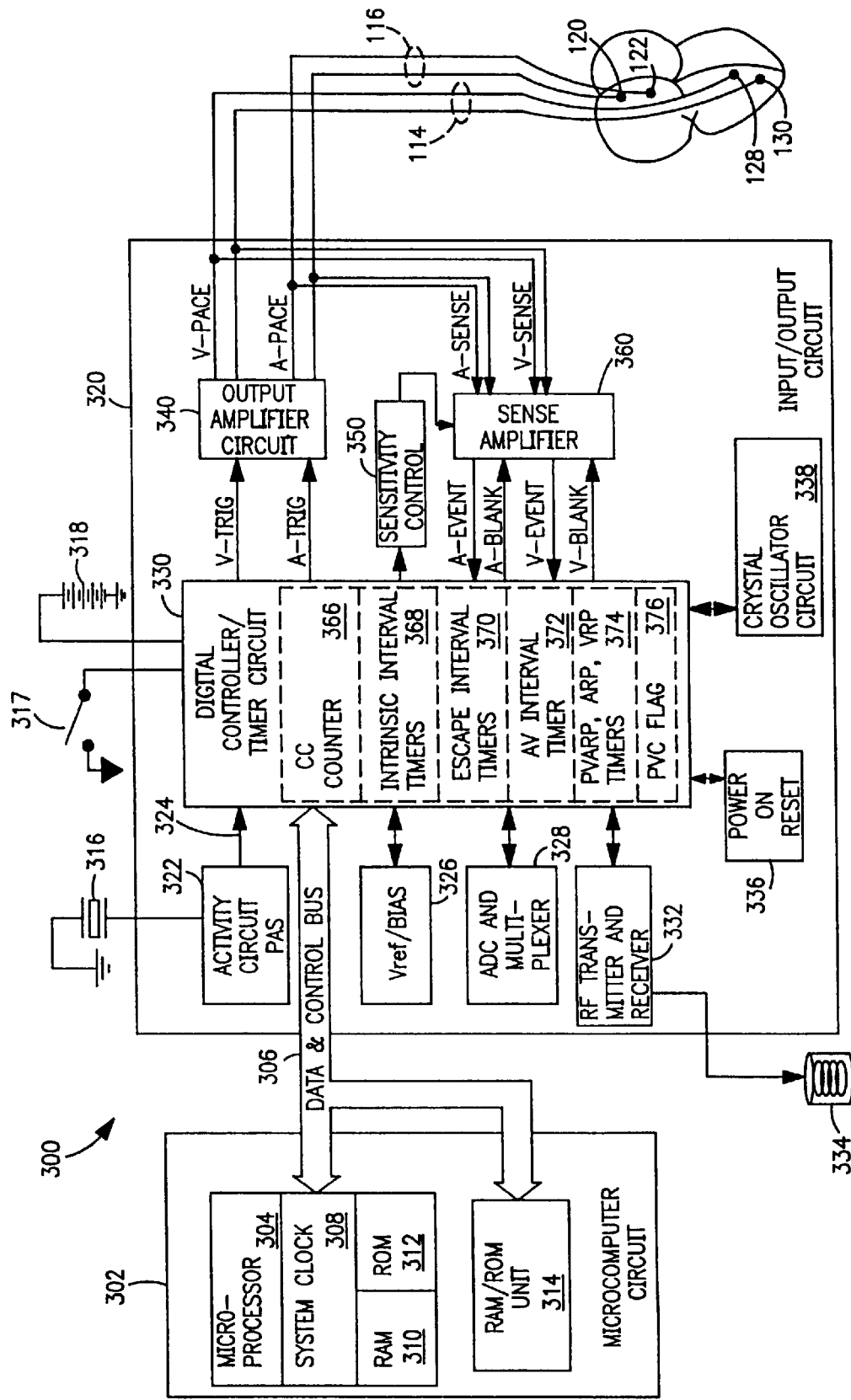
FIG. 2 is a schematic block diagram of major functional blocks of one embodiment of a pacemaker operating system that can be employed in accordance with the present invention to carry out the timing of an appropriate PVARP in response to a PVC or other AV synchrony disrupting event to avoid persistent loss of AV synchrony.

The IPG 100 is provided with a hermetically sealed enclosure 118, typically fabricated of bio-compatible metal such as titanium, enclosing the dual chamber IPG circuit 300 depicted in FIG. 2. A connector block assembly 112 is mounted to the top of the enclosure 118 to receive electrical connectors located on the proximal connector ends of the depicted bipolar atrial and ventricular pacing leads 114 and 116.

The bipolar atrial pacing lead 116 extends between its proximal connector coupled to IPG 100 and distal atrial pace/sense electrodes 120 and 122 located in the right atrium 12 of heart 10 to sense P-waves and to deliver atrial pacing pulses to the right atria. Atrial pacing pulses may be delivered between electrodes 120 and 122 in a bipolar pacing mode or between electrode 122 and the housing 118 of the IPG 100 in a unipolar pacing mode. Sensing of P-waves may occur between electrode 120 and electrode 122 in a bipolar sensing mode or between either of electrode 120 and 122 and the housing 118 of the IPG 100 in a unipolar atrial sensing mode.

Similarly, the bipolar ventricular pacing lead 114 extends between its proximal connector coupled to IPG 100 and distal ventricular pace/sense electrodes 128 and 130 located in the right ventricle 16 of heart 10 to both sense R-waves and to deliver ventricular pacing pulses to the ventricles. Ventricular pacing pulses may be delivered between electrodes 128 and 130 in a bipolar pacing mode or between electrode 130 and the housing 118 of the IPG 100 in a unipolar pacing mode. Sensing of R-waves may occur between electrodes 128 and 130 in a bipolar sensing mode or between either of electrode 128 and 130 and the housing 118 of the IPG 100 in a unipolar ventricular sensing mode.

In accordance with a preferred embodiment of the invention, the IPG 100 or one of the leads 114 or 116 includes one or more physiologic sensor that is employed to derive a physiologic signal that relates to the need for cardiac output. The use of physiologic sensors to provide variation of pacing rate in response to sensed physiologic parameters, such as physical activity, oxygen saturation, blood pressure and respiration, has become commonplace. Commonly assigned U.S. Pat. Nos. 4,428,378 and 4,890,617, incorporated herein by reference in their entireties, disclose activity sensors which are employed to vary the pacing escape interval in single and dual chamber pacemaker IPGs in response to sensed physical activity. Such an activity sensor 316 is coupled to the inside surface of the IPG housing 118 and may take the form of a piezoelectric crystal transducer as is well known in the art.

Typically, the AV delay in modern VDD, VDDR, DDD and DDDR pacemakers is either fixed or varies with the prevailing intrinsic atrial rate, measured as an A-A interval, and/or varies as a function of a physiologic sensor derived pacing rate. The variation of the AV delay as a function of the atrial escape interval in early AV synchronous pacemakers is disclosed, for example, in U.S. Pat. No. 4,108,148, incorporated herein by reference. The variation of the AV interval as a function of a sensed physiologic signal or an atrial escape interval pacing rate derived therefrom is disclosed in U.S. Pat. Nos. 4,303,075 and 5,024,222, all incorporated herein by reference.

The IPG circuit 300 within IPG 100 and the bipolar atrial and ventricular leads 114 and 116 are depicted in FIG. 2 in relation to heart 10. The IPG circuit 300 is divided generally into a microcomputer circuit 302 and a pacing input/output circuit 320. The inpuvoutput circuit 320 includes the digital controller/timer circuit 330, the atrial and ventricular pacing pulse output circuit 340 and the atrial and ventricular sense amplifier circuit 360, as well as a number of other components and circuits described below. Control of timing and other functions within the inpu/output circuit 320 is provided by the digital controller/timer circuit 330. Digital controller/timer circuit 330, operating under the general control of the microcomputer circuit 302, includes a set of timing and associated logic circuits, of which certain ones pertinent to the present invention are depicted and described further below.

The atrial and ventricular pacing pulse output circuit 340 and sense amplifier circuit 360 contain pulse generators and sense amplifiers corresponding to any of those presently employed in commercially marketed cardiac pacemakers for atrial and ventricular pacing and sensing. The bipolar leads 114 and 116 are illustrated schematically with their associated electrode sets 120, 122 and 128, 130, respectively, as coupled directly to the atrial and ventricular pacing pulse output circuit 340 and sense amplifier circuit 360 of pacing circuit 320.

Digital controller/timer circuit 330 also controls sensitivity settings of the atrial and ventricular sense amplifiers 360 by means of sensitivity control 350 and times out an atrial blanking (A-BLANK) signal and a ventricular blanking (V-BLANK) signal. In the absence of an A-BLANK signal, atrial depolarizations or P-waves that are detected by the atrial sense amplifier result in an A-SENSE signal that is communicated to the digital controller/timer circuit 330. Similarly, in the absence of a V-BLANK signal, ventricular depolarizations or R-waves that are detected by the ventricular sense amplifier result in a V-SENSE signal that is communicated to the digital controller/timer circuit 330. The A-SENSE signal is characterized as a refractory A-SENSE signal if it occurs during time-out of an ARP or a PVARP or a non-refractory A-SENSE signal if it occurs after time-out of these atrial refractory periods. Similarly, a V-SENSE signal is characterized as a refractory V-SENSE signal if it occurs during time-out of a VRP or a non-refractory V-SENSE signal if it occurs after time-out of this ventricular refractory period. Refractory A-SENSE signals and V-SENSE signals are typically ignored for purposes of resetting timed out AV delays and V-A intervals, although diagnostic data may be accumulated related to their occurrences.

Digital controller/timer circuit 330 also interfaces with other circuits of the input output circuit 320 or other components of IPG circuit 300. Crystal oscillator circuit 338 provides the basic timing clock and battery 318 provides power for the pacing circuit 320 and the microcomputer circuit 302. Power-on-reset circuit 336 responds to initial connection of the circuit to the battery 318 for defining an initial operating condition and similarly, resets the operative state of the IPG circuit 300 in response to detection of a low battery condition. Reference mode circuit 326 generates stable voltage reference and currents for the analog circuits within the pacing circuit 320. ADC (analog to digital converter) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

Data transmission to and from an external programmer (not shown) is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGM's of atrial and/or ventricular electrical activity and Marker Channel pulses indicating the occurrence of sensed and paced depolarizations in the atrium and ventricle, as are well known in the pacing art. The telemetry transceiver system disclosed in commonly assigned U.S. Pat. No. 5,354,319, incorporated herein by reference, may be employed to provide the uplink and downlink telemetry from and to the implanted medical device in the practice of the present invention.

Reed switch 317 when closed by application of a magnetic field may be employed to enable programming of the pacemaker and also may be employed to convert the pacemaker temporarily to an asynchronous pacing mode such as DOO or VOO. Operation in the asynchronous mode may continue as long as the magnetic field is present, may continue until overridden by the programmer or may continue for a pre-set time period.

The activity sensor 316 generates an output signal in response to certain patient activities, e.g. ambulating, that is processed and used as a rate control parameter (RCP). If the IPG operating mode is programmed to a rate responsive mode, the patient's activity level developed in the patient activity circuit (PAS) 322 is monitored, and a sensor derived V-A, A-A or V-V interval is derived proportionally thereto. A timed interrupt, e.g., every two seconds, may be provided in order to allow the microprocessor 304 to analyze the output of the activity circuit PAS 322 and update the basic V-A (or A-A or V-V) escape interval employed to govern the pacing cycle and to adjust other time intervals as described below.

Microcomputer 202 contains a microprocessor 304 and associated system clock 308 and on-processor RAM and ROM chips 310 and 312, respectively. In addition, microcomputer circuit 302 includes a separate RAM/ROM chip 314 to provide firmware and additional RAM memory capacity. Microprocessor 304 is interrupt driven, operating in a reduced power consumption mode normally, and awakened in response to defined interrupt events, which may include the A-TRIG, V-TRIG, A-SENSE and V-SENSE signals.

Microcomputer 302 controls the operational functions of digital controller/timer 324, specifying which timing intervals are employed in a programmed pacing mode via data and control bus 306. The specific values of the intervals timed by the digital controller/timer circuit 330 are controlled by the microcomputer circuit 302 by means of data and control bus 306 from programmed-in parameter values. The microcomputer 302 also calculates the RCP derived or intrinsic atrial rate derived V-V, A-A or V-A interval, the variable AV delay, and the variable ARP, PVARP and VRP.

In the embodiment illustrated the microcomputer 302 detects the occurrence of events which my be disruptive of AV synchrony and correspondingly controls the duration of the PVARP. However, the same result may of course be accomplished using custom digital circuitry such as resides in the controller/timer circuit to vary the PVARP, in a manner analogous to the use of custom digital circuitry in prior art pacemakers to extend PVARPs in response to PVCs, for example as disclosed in U.S. Pat. No. 5,103,820 issued to Markowitz, incorporated heroin by reference in its entirety.

The depicted counters and timers within digital controller/timer circuit 330 include a cardiac cycle (CC) counter 366, intrinsic interval timers 368 for timing average intrinsic A-A and V-V intervals from A-SENSEs and V-SENSEs, escape interval timers 370 for timing A-A, V-A, and/or V-V pacing escape intervals, an AV delay timer 372 for timing the SAV delay from a preceding A-SENSE or PAV delay from a preceding A-TRIG, refractory period timers 374 for timing ARP, PVARP and VRP times and a PVC flag register 376 that is set upon detection of a PVC. Digital controller/timer circuit 330 starts and times out these intervals and time periods that are calculated by microcomputer circuit 302 for controlling the above-described operations of the atrial and ventricular sense amplifiers in sense amplifier circuit 360 and the atrial and ventricular pace pulse generators in output amplifier circuit 340.

In order to trigger generation of a V-PACE pulse, digital controller/timer circuit 330 generates a V-TRIG signal at the end of a PAV or SAV delay provided by AV delay timer 372. Similarly, in order to trigger an atrial pacing or A-PACE pulse, digital controller/timer circuit 330 generates an A-TRIG signal at the termination of the V-A interval timed out by escape interval timers 370. Typically, digital controller/timer circuit 330 also times out associated intervals including the A-BLANK interval following delivery of an A-TRIG pulse or V-TRIG pulse, during which atrial sensing is disabled, as well as the V-BLANK interval following a V-TRIG atrial pulse, during which ventricular sensing is disabled.

The refractory period timers 374 time the ARP from an A-TRIG pulse or A-SENSE during which a sensed A-SENSE is ignored for the purpose of resetting the V-A interval. The ARP extends from the beginning of the SAV or PAV interval following either an A-SENSE or an A-TRIG and until a predetermined time following a V-SENSE or a V-TRIG. The refractory period timers 374 also time the PVARP from a V-TRIG pulse or V-SENSE during which a sensed A-SENSE is also ignored for the purpose of resetting the V-A interval. The VRP is also be timed out by the refractory period timers 374 after a V-SENSE or V-TRIG signal so that a subsequent, closely following V-SENSE is ignored for the purpose of restarting the V-A interval and setting the PVC flag in register 366.

The base ARP, PVARP and VRP that prevails at the lower rate of 60–70 bpm, for example, are either default or programmed parameter values stored in the microcomputer 302. These refractory period parameter values can be fixed for the full operating range of pacing rates between the lower rate and the URL, which may be 120 bpm, for example, or they can be programmed to follow the algorithm for automatically shortening in duration as the paced or intrinsic heart rate increases to ensure that the long refractory periods during the diminishing escape intervals do not prevent delivery of ventricular pacing pulses synchronized to valid intrinsic P-waves. In conjunction with rate or sensor varied PVARPs, it has become commonplace to program the longest available PVARP as the base PVARP to reduce the incidences or possibility of triggering a PMT upon sensing a PVC, and this in turn can lead to the persistent loss of synchrony to the underlying intrinsic P-waves following a PVC.

The illustrated IPG circuit 300 of FIG. 2 is merely exemplary, and corresponds to the general functional organization of most multi-programmable microprocessor controlled DDD and DDDR cardiac pacemaker IPGs presently commercially available. It is believed that the present invention is most readily practiced in the context of such an IPG, and that the present invention can therefore readily be practiced using the basic hardware of existing microprocessor controlled dual chamber pacemakers, as presently available, with the invention implemented primarily by means of modifications to the software stored in the ROM 310 of the microcomputer circuit 302. However, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacemaker IPG having an architecture as illustrated in FIG. 2, and a circuit architecture as illustrated in FIG. 2 is not believed to be a prerequisite to enjoying the benefits of the present invention.

Figure 3:
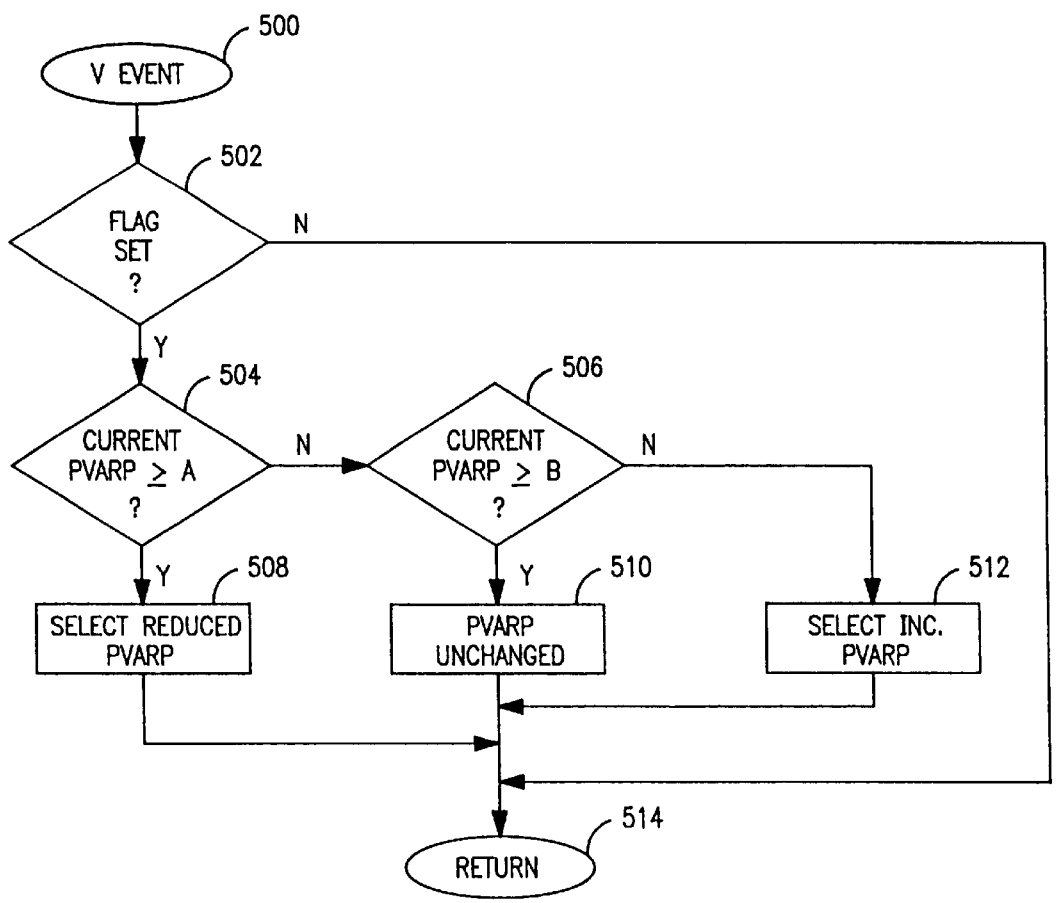
FIG. 3 is a general flow chart illustrating operation of a device in accordance with the present invention.
Figure 4:
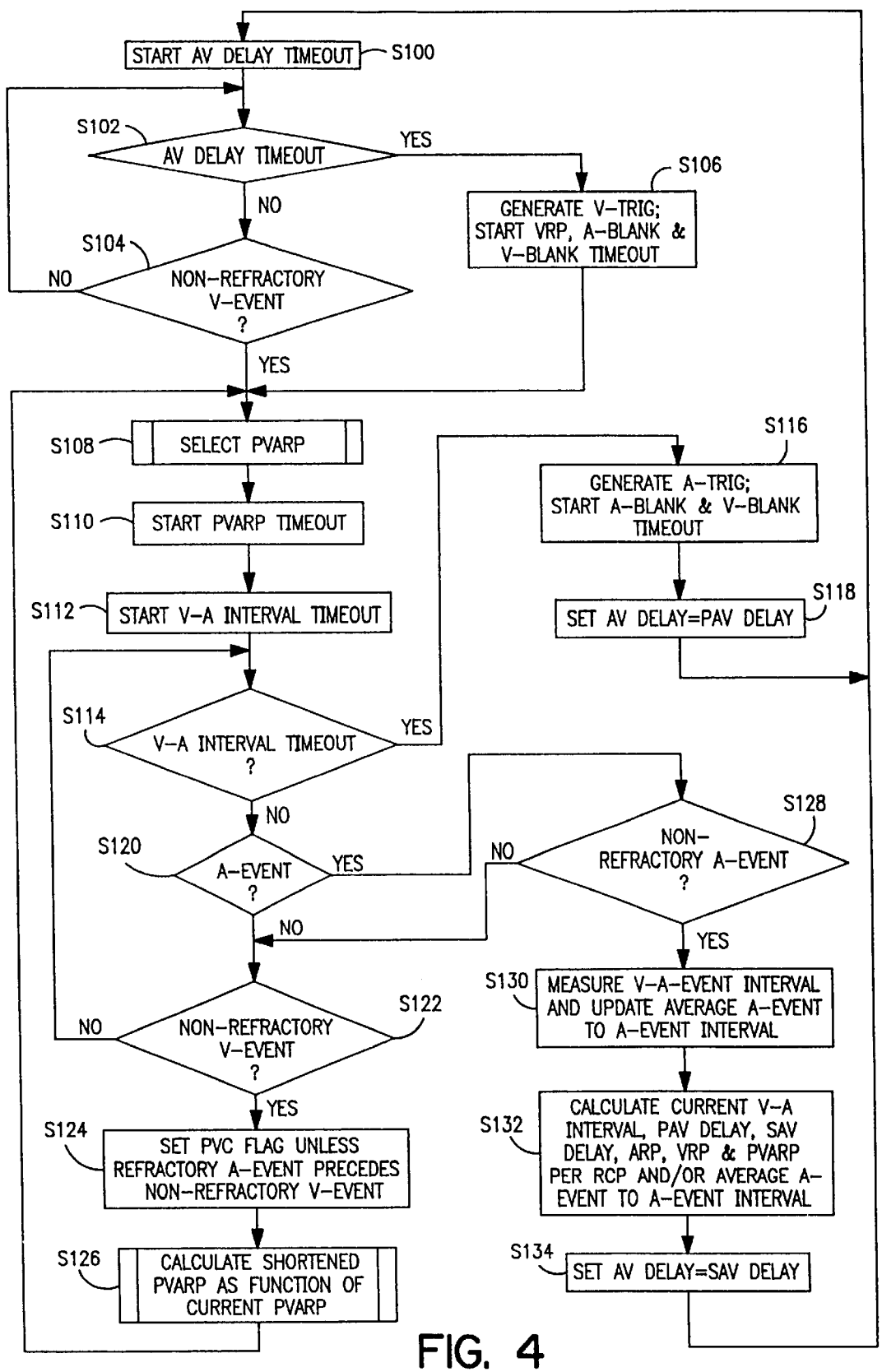
FIG. 4 is a more detailed flow chart illustrating the operation of a device according to the present invention, focusing specifically on the response of the device to a PVC.
Figure 5:
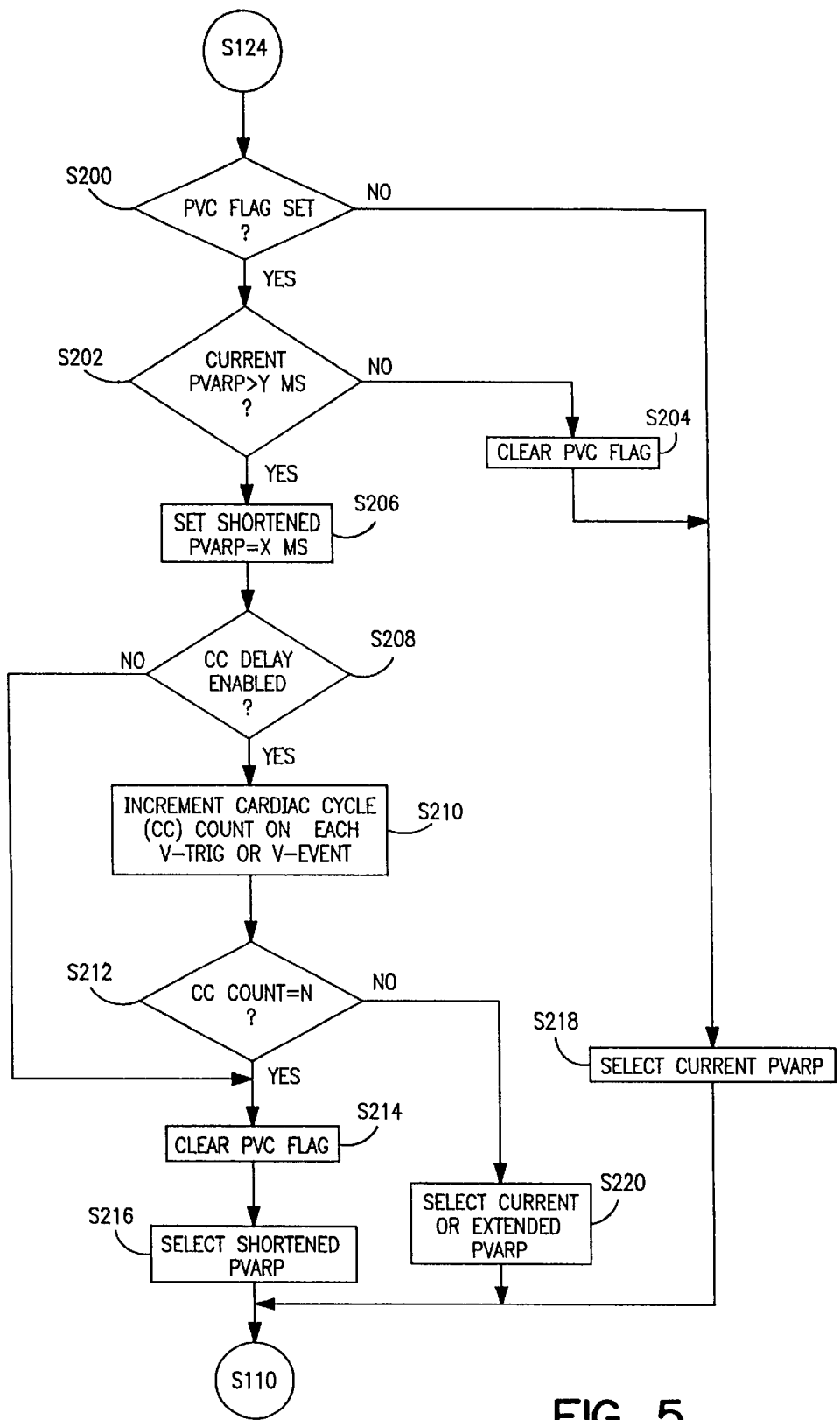
FIG. 5 is a flow chart illustrating the method of selection of an appropriate PVARP in accordance with the present invention.
Figure 6A:
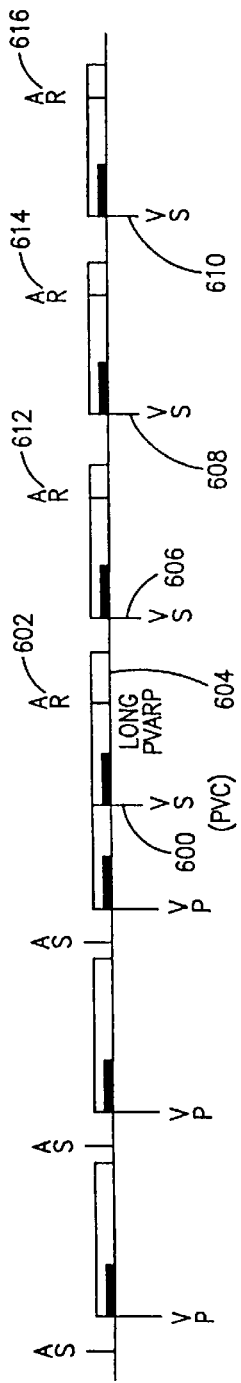
FIGS. 6A–6C are timing diagrams illustrating the situation in which a PVC leads to persistent loss of AV synchrony and the operation of the present invention in response to a PVC in similar circumstances.

FIGS. 3–5 are flow charts illustrating the operation of a pacemaker according to the present invention. To understand the operation of the invention, it is worthwhile to review the operation of a device according to the prior art as illustrated in FIG. 6A. FIG. 6A depicts a series of cardiac cycles that switch from the normal AS-VP (atrial sense—ventricular pace) sequence in which AV synchrony is maintained to the situation in which persistent loss of AV synchrony results from a PVC. As illustrated, a ventricular sense (VS) 600 occurs during the timeout of the V-A interval of the third cardiac cycle and is thus identified as a PVC. The subsequent spontaneous atrial depolarization (AR) 602 falls within the PVARP 604 following the PVC and is disassociated from the subsequent ventricular depolarization (VS) 606 following the PVC. If the current PVARP in effect following the ventricular depolarizations 606, 608, 610 is long enough, the following intrinsic atrial depolarizations (AR) 612, 614, 616 will occur within PVARPs, as illustrated. Therefore, no A-V delays will be initiated and no atrial-synchronized ventricular pacing will occur. If the device defines ventricular depolarizations sensed during the V-A interval as PVCs, the situation may be worsened, as prolonged PVARPs may continue to be employed. The same result may of course occur even if the PVARP is not extended following the PVC and/or subsequent ventricular depolarizations if the current PVARP is of sufficient length. The inhibition of ventricular pacing can continue indefinitely as long as the dissociation between the intrinsic atrial rate and the intrinsic ventricular rate continues, with the possible result of insufficient cardiac output.

FIG. 3 is a general functional flow chart illustrating the overall operation of the device according to the present invention to control the duration of the PVARP in response to an event which disrupts AV synchrony. On occurrence of ventricular event 500 which may either be a delivered ventricular pacing pulse or a sensed ventricular depolarization, the device checks to determine whether a flag has previously been set indicating the occurrence of an event which might disrupt AV synchrony. For example, the disrupting event may be the ventricular event 500 itself, if the ventricular event is identified as a PVC. Alternatively, the flag may indicate that the ventricular event occurred immediately following a change in pacing mode or change in pacemaker operation due to programming, application or removal of a magnet, exit from noise reversion mode, or other event capable of disrupting AV synchrony. If no flags are set, the device simply continues with normal operation at 514 and initiates the various time intervals and periods discussed above, including the AV delay or V-A escape interval and the PVARP as currently specified.

If the device determines at 502 that a flag indicating the occurrence of an event disruptive of AV synchrony is set, the device checks to determine whether the current setting of the PVARP is greater than a first defined duration "A". If so, the device selects a reduced PVARP duration which may either be a predefined duration or may be calculated as a function of the current PVARP duration. For example, the PVARP may be decreased by a defined decrement duration or a defined percentage of the current PVARP duration. The device would then return to normal operation at 514, restoring the current PVARP.

Although the flow chart of FIG. 3 reflects the premise that if a shortened PVARP is selected it will apply to the PVARP following the ventricular event at 500, it should be understood that in the context of the selection of a reduced PVARP at 508, employment of the reduced PVARP value may await the next subsequent ventricular event following that occurring at 500, as discussed above.

In some embodiments, in the event that the current PVARP duration is less than the first defined duration "A" the device may optionally check at 506 to determine whether the current setting of PVARP exceeds a second defined duration "B" which is less than the first defined duration "A". If so, the device leaves the PVARP unchanged at 510 and continues to operate normally at 514 as discussed above. On the other hand, if the current duration of the PVARP is less than the second defined duration "B", the device may extend the PVARP at 512 in order to prevent the possibility of pacemaker mediated tachycardias.

In its simplest form, the invention may be practiced by simply setting the PVARP following any event which disrupts AV synchrony to a pre-defined duration less than the maximum PVARP values allowable for the pacemaker. In this fashion, if the present PVARP is excessively long, the PVARP will be shortened in response to the disrupting event. In this embodiment no comparison of the current PVARP to a defined duration is required.

FIG. 4 is a functional flow chart of the overall pacing cycle timing operation of the pacemaker IPG illustrated in FIG. 2 in the DDD or DDDR pacing modes. In the flow chart of FIG. 4, it is assumed that the A-A or V-V escape interval, cardiac cycle timing of the IPG ranges between a programmed lower rate and a programmed upper rate limit (URL) and is based on the definition of a V-A interval and an AV delay, specifically either the SAV or the PAV interval. The AV delay and V-A interval of any given pacing cycle may be determined as a function of a sensor-derived V-A interval (SVA) or an atrial rate based V-A interval determined by the average measured intrinsic A-A atrial rate if it is stable and varies between the programmed lower rate and URL. The operations of the flow chart may also incorporate any of the mode switching and sinus preference algorithms of the prior art described above to switch between the use of the sensor or the atrial rate derived escape intervals. However the algorithm is specifically implemented, it is understood to incorporate the PVARP setting algorithm of the present invention as described hereafter.

Moreover, it is also assumed that the ARP, VRP and PVARP are either fixed in duration or are programmed to base intervals correlated with the programmed lower rate. In the latter case, at least the PVARP may be programmed to decrease in length as the A-A or V-V escape interval decreases while either tracking an increasing sensor derived or sinus atrial rate. Because of this varying PVARP capability, it has become common to program the base PVARP to the maximum length, e.g. 400 ms or more, to minimize PMT. The steps depicted in FIG. 4 set forth the primary timing functions and actions of the IPG circuit 300 which recycle continuously. The steps of FIG. 4 and FIG. 5 set forth the response to a PVC or other disrupting event that shortens the PVARP particularly when the PVARP is greater than a defined duration.

At step S100, the V-A interval being timed out in step S114 is reset in response to a non-refractory A-SENSE in step S128 or an A-TRIG in step S116, and timing of the current PAV or SAV delay is commenced. During step S100, the system awaits either time out of the current AV delay (which may be a PAV or SAV) in step S102 or a non-refractory V-SENSE in step S104. A V-TRIG and the associated A-BLANK and V-BLANK are generated at step S106 at the end of the AV delay if a non-refractory V-SENSE does not occur at step S104 prior to AV time-out in step S102.

A PVARP is selected in step S108 when the non-refractory V-SENSE occurs in step S104 or the V-TRIG occurs in step S106. Timing out of the PVARP is started in step S110, and timing out of the V-A interval is started in step S112. The selection of the PVARP is dependent upon the calculation of the PVARP in step S126, and these steps S108 and S126 are shown in expanded detail in FIG. 5 and described further below. The V-A interval started in step S112 is either the sensor-derived V-A interval or the average intrinsic atrial rate derived V-A interval that is calculated in step S132.

The algorithm awaits expiration of the V-A interval at step S114, and it is possible that a refractory or non-refractory A-SENSE or V-SENSE can occur during the V-A interval time-out. An A-TRIG signal is generated in step S116 at the end of the V-A interval if the V-A interval times out without sensing any such intervening non-refractory A-SENSE or V-SENSE. In this case, the next succeeding AV delay is defined to be equal to PAV at step S118, and the AV timing is commenced again at step S100.

If an A-SENSE is sensed in step S120 during the V-A interval, it is determined to be refractory or non-refractory in step S128, and a non-refractory A-SENSE terminates the V-A interval and restarts the AV delay in step S100. If the A-SENSE is determined to occur after time-out of the PVARP, it is characterized as non-refractory in step S128. The non-refractory A-SENSE causes the V-A interval to be measured by intrinsic interval timer 368 and employed in step S130 to derive or update the intrinsic atrial rate that is saved in RAM. The V-A interval, the SAV and PAV delays and the pacing escape interval for the next cardiac cycle are recalculated in step S132 in dependence upon either the updated average A-A interval or upon the RCP in a manner well known in the art. The current PVARP is derived in this step which, as noted above, varies in length with the derived pacing escape interval. In step S134, the AV delay is set to the recalculated SAV delay, and the AV delay time-out is restarted in step S100.

If a non-refractory V-SENSE is sensed at step S122 during time out of the V-A interval in the absence of detection of a preceding refractory A-SENSE, the sensed event is characterized as a PVC in step S124. Alternatively but less desirably any non-refractory sensed ventricular depolarization may be characterized as a PVC. In either case, if the PVC flag is set in step S124, it is necessary to calculate the appropriate PVARP in step S126 and to select it in step S108. As described in conjunction with FIG. 5, as part of the calculation and selection steps S126 and S108, the device may also check in addition or in the alternative to determine if any other flag is set indicative of any of the other events described above capable of disrupting AV synchrony, and the device in response may proceed to calculate and select the PVARP in the same manner.

The calculation and selection of the PVARP in steps S126 and S108 are depicted in greater detail in steps S200–S212 of FIG. 5. At step S200, the PVC flag (and/or other event flags) is checked, and if no flag is set, then the current fixed PVARP that is programmed or the current variable PVARP calculated in step S132 is selected in step S216 and started in step S110.

If the PVC flag (and/or other event flag) is set as determined in step S200, then the length of the current PVARP is examined in step S202 by comparing it to a programmed duration "Y", e.g., 250 ms. If it is already less than "Y", then the PVC flag is cleared in step S204 and the current PVARP is also selected in step S216.

However, if the current PVARP is greater than "Y", then the shortened PVARP is defined as "X" ms in step S206. The shortened PVARP can be derived in a number of ways. For example, it can be a programmed fixed duration or the shortest PVARP that is normally employed at the upper pacing rate limit or may simply be set equal to "Y". Alternatively, it can be derived from the current PVARP e.g., by subtraction of an offset value or by calculation of a programmable percentage of the current PVARP determined in step S132.

Figure 6B:
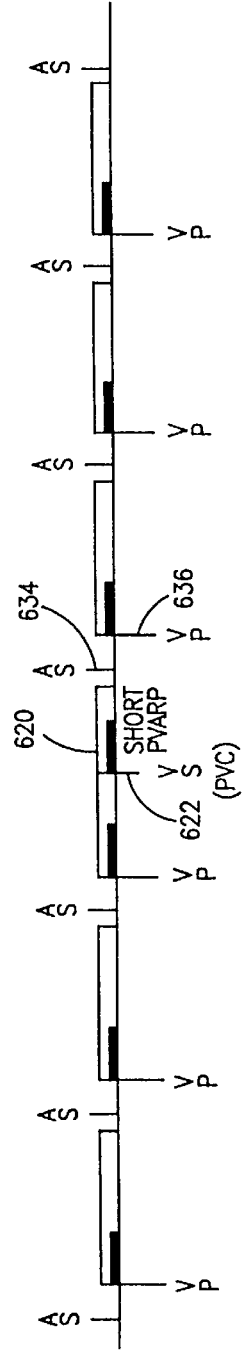
Figure 6C:
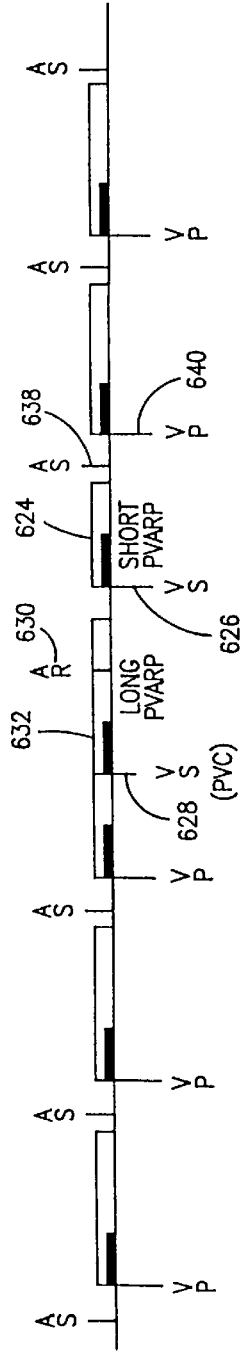

Then, it is necessary to determine if the shortened PVARP is to be applied immediately starting with the immediately preceding ventricular event as shown in FIG. 6B or is to be delayed until the next or another subsequent ventricular event, e.g., a V-SENSE or V-TRIG as shown in FIG. 6C. In accordance with one aspect of the present invention, the shortened PVARP 620 (FIG. 6B) can be applied either immediately when a disruptive event occurs, i.e., following the ventricular event 622 (FIG. 6B) in conjunction with which the flag or flags were checked or the shortened PVARP 624 (FIG. 6C) may be applied to start following the ventricular event 626 (FIG. 6C) initiating a cardiac cycle (CC) that is subsequent to the ventricular event 628 (FIG. 6C) which is or immediately follows the disrupting event. The subsequent ventricular event may itself satisfy PVC detection rules if it is not preceded by a refractory or non-refractory A-SENSE or it may simply be a V-PACE or V-SENSE that is preceded by a non-refractory or refractory A-SENSE, e.g., the AR event 630 depicted in FIG. 6C.

The selection of when the shortened PVARP is to be employed can be programmed by enabling the CC delay in step S208 and programming a CC count threshold "N", for step S212, where N>1. If the CC delay is not enabled in step S208, then the PVC flag is cleared in step S214 and the shortened PVARP is immediately selected in step S216 as illustrated at 620 in the third cardiac cycle of FIG. 6B.

However, if the cardiac cycle delay is enabled in step S208, then N is set to "2", for example. The CC count is initialized at "1" by reading the set PVC or other flag in step S200 and awaits being incremented to "2" on the next V-SENSE or V-TRIG in step S208. In the meantime, the CC count of "1" is compared to "2" (N) in step S212, and either the current PVARP or an extended PVARP, as illustrated at 632 (FIG. 6C) is selected in step S220 to be started coincidentally with the ventricular event 628 (FIG. 6C) which is or immediately follows the disrupting event. The current or extended PVARP length renders the subsequent atrial event a refractory A-SENSE (AR) as illustrated at 630 in FIG. 6C. The CC count is incremented in step S210 to "2" at the V-TRIG in step S106 or V-SENSE in step S104 starting the next cardiac cycle.

When the condition of step S212 is then satisfied, the PVC or other flag is cleared in step S214, and the shortened PVARP set in step S206 is selected in step S216. Atrial tracking is restored in the subsequent cardiac cycles as shown at 634 and 638 in FIG. 6B and at 638 and 640 in FIG. 6C.

FIGS. 6B and 6C depict the shortened PVARP applied for a single immediate or delayed cardiac cycle. Alternatively, the shortened PVARP can be incrementally increased in length over a number of cardiac cycles back to an appropriate current PVARP for the prevailing sinus heart rate or the sensor determined heart rate. The values of the various pacemaker defined intervals and time periods including the atrial rate dependent PVARP or the sensor related PVARP, the shortened PVARP, the ARP, the VRP, the PAV and SAV delays, and the V-A intervals are derived in the steps of FIGS. 4 and 5 by operating algorithms or look up table values stored in either ROM or RAM that are fetched and used by the microprocessor as described above.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A method of employing a pacemaker to pace a patient's heart, comprising:
   responsive to ventricular events, defining a post ventricular atrial refractory period having a first duration;
   detecting atrial depolarizations;
   responsive to detected atrial depolarizations outside of the post ventricular refractory period, timing an atrial-ventricular (AV) delay;
   delivering a ventricular pacing pulse upon expiration of an AV delay;
   detecting events which may disrupt AV synchrony; and
   responsive to detection of an event which may disrupt AV synchrony,
   comparing the first duration to a defined duration; and
   defining a post ventricular atrial refractory period having a second duration less than the first duration if the first duration is greater than or equal to the defined duration.

2. The method of claim 1, wherein defining the post ventricular atrial refractory period having a first duration comprises
   determining atrial heart rate from sensed atrial depolarizations and
   defining the first duration in proportion to the determined atrial rate.

3. The method of claim 1, wherein defining a post ventricular atrial refractory period having a second duration comprises defining the second duration as a function of the first duration.

4. The method of claim 1, wherein defining a post ventricular atrial refractory period having a second duration comprises defining the second duration as a fixed value.

5. The method of claim 1 or claim 2 or claim 3 or claim 4 wherein detecting events which may disrupt AV synchrony comprises detecting premature depolarizations of the patient's heart.

6. The method of claim 5 wherein detecting events which may disrupt AV synchrony comprises detecting PVCs.

7. The method of claim 1 or claim 2 or claim 3 or claim 4 wherein detecting events which may disrupt AV synchrony comprises detecting changes in pacing mode of the pacemaker from a non-atrial synchronized mode to an atrial synchronized mode.

8. The method of claim 1 or claim 2 or claim 3 or claim 4 wherein detecting events which may disrupt AV synchrony comprises detecting a magnetic field.

9. The method of claim 1 or claim 2 or claim 3 or claim 4 wherein detecting events which may disrupt AV synchrony comprises detecting operation of pacemaker telemetry.

10. The method of claim 1, wherein defining a post ventricular atrial refractory period having a second duration comprises initiating the post ventricular atrial refractory period having the second duration responsive to a ventricular event which may disrupt AV synchrony.

11. The method of claim 1, wherein defining a post ventricular atrial refractory period having a second duration comprises initiating the post ventricular atrial refractory period having a second duration responsive to a ventricular event which immediately follows an event which may disrupt AV synchrony.

12. The method of claim 1, wherein defining a post ventricular atrial refractory period having a second duration comprises initiating the post ventricular atrial refractory period having a second duration responsive to a later ventricular event subsequent to a ventricular event which may disrupt AV synchrony.

13. The method of claim 1, wherein defining a post ventricular atrial refractory period having a second duration comprises initiating the post ventricular atrial refractory period having a second duration responsive to a later ventricular event which is subsequent to a ventricular event which immediately follows an event which may disrupt AV synchrony.

14. A pacemaker, comprising:
   means responsive to ventricular events, for defining a post ventricular atrial refractory period having a first duration;
   an atrial amplifier providing atrial sense signals responsive to atrial depolarizations;
   timing means responsive to atrial sense signals outside of the post ventricular refractory period, for timing an atrial-ventricular (AV) delay;

a ventricular pulse generator providing a ventricular pacing pulse responsive to expiration of an the AV delay;

means for detecting events which may disrupt AV synchrony; and means responsive to detection of an event which may disrupt AV synchrony for comparing the first duration to a defined duration and for defining a post ventricular atrial refractory period having a second duration less than the first duration if the first duration is greater than or equal to the defined duration.

15. The pacemaker of claim 14, wherein the means for defining the post ventricular atrial refractory period having a first duration comprises:

means for determining atrial heart rate from sensed atrial depolarizations; and means for defining the first duration in proportion to the determined atrial rate.

16. The pacemaker of claim 14, wherein the means for defining a post ventricular atrial refractory period having a second duration comprises means for defining the second duration as a function of the first duration.

17. The pacemaker of claim 14, wherein the means for defining a post ventricular atrial refractory period having a second duration comprises means for defining the second duration as a fixed duration.

18. The pacemaker of claim 14 or claim 15 or claim 16 or claim 17 wherein the means for detecting events which may disrupt AV synchrony comprises means for detecting premature depolarizations of the patient's heart.

19. The pacemaker of claim 18 wherein the means for detecting events which may disrupt AV synchrony comprises means for detecting PVCs.

20. The pacemaker of claim 14 or claim 15 or claim 16 or claim 17 wherein the means for detecting events which may disrupt AV synchrony comprises means for detecting changes in pacing mode of the pacemaker from a non-atrial synchronized mode to an atrial synchronized mode.

21. The pacemaker of claim 14 or claim 15 or claim 16 or claim 17 wherein the means for detecting events which may disrupt AV synchrony comprises means for detecting a magnetic field.

22. The pacemaker of claim 14 or claim 15 or claim 16 or claim 17 wherein the means for detecting events which may disrupt AV synchrony comprises means for detecting operation of pacemaker telemetry.

23. The pacemaker of claim 14, wherein the means for defining a post ventricular atrial refractory period having a second duration comprises means for initiating the post ventricular atrial refractory period having a second duration responsive to a ventricular event which may disrupt AV synchrony.

24. The pacemaker of claim 14, wherein the means for defining a post ventricular atrial refractory period having a second duration comprises means for initiating the post ventricular atrial refractory period having the second duration responsive to a ventricular event which immediately follows an event which may disrupt AV synchrony.

25. The pacemaker of claim 14, wherein the means for defining a post ventricular atrial refractory period having a second duration comprises means for initiating the post ventricular atrial refractory period having the second duration responsive to a later ventricular event subsequent to a first ventricular event which may disrupt AV synchrony.

26. The pacemaker of claim 14, wherein the means for defining a post ventricular atrial refractory period having a second duration comprises means for initiating the post atrial ventricular refractory period having the second duration responsive to a later ventricular which is subsequent to a first ventricular event which immediately follows an event which may disrupt AV synchrony.

* * * * *

UNITED STATES PATENT AND TRADEMARK OFFICE
CERTIFICATE OF CORRECTION

PATENT NO.   : 6,311,088 B1
DATED        : October 30, 2001
INVENTOR(S)  : Betzold et al.

It is certified that error appears in the above-identified patent and that said Letters Patent is hereby corrected as shown below:

<u>Title page,</u>
Item [57], ABSTRACT,
Line 7, delete "a."

<u>Column 15,</u>
Line 2, delete "an."

<u>Column 16,</u>
Line 33, after "ventricular" insert -- event --.

Signed and Sealed this

Twenty-eighth Day of January, 2003

JAMES E. ROGAN
*Director of the United States Patent and Trademark Office*